US006528450B2

(12) United States Patent
Wu et al.

(10) Patent No.: US 6,528,450 B2
(45) Date of Patent: Mar. 4, 2003

(54) CATALYST COMPOSITION AND PROCESSES THEREFOR AND THEREWITH

(75) Inventors: An-hsiang Wu, Bartlesville, OK (US); Charles A. Drake, Nowata, OK (US)

(73) Assignee: Phillips Petroleum Company, Bartlesville, OK (US)

(*) Notice: Subject to any disclaimer, the term of this patent is extended or adjusted under 35 U.S.C. 154(b) by 90 days.

(21) Appl. No.: 09/255,973

(22) Filed: Feb. 23, 1999

(65) Prior Publication Data

US 2002/0016258 A1 Feb. 7, 2002

Related U.S. Application Data

(63) Continuation-in-part of application No. 08/697,767, filed on Aug. 29, 1996, now abandoned.

(51) Int. Cl.$^7$ .......................... B01J 21/08; B01J 21/12; B01J 21/14; B01J 27/19; B01J 23/00
(52) U.S. Cl. .................. 502/240; 502/208; 502/211; 502/255; 502/258; 502/259; 502/260; 502/263; 502/314; 502/315; 502/322; 502/327; 502/332; 502/335; 502/337
(58) Field of Search ................... 502/305, 308, 502/309, 313, 314, 315, 319, 320, 321, 322, 323, 325, 326, 327, 332, 333, 334, 337, 335, 339, 349, 350, 351, 208, 210, 211, 214, 232, 240, 254, 255, 256, 258, 259, 260, 263

(56) References Cited

U.S. PATENT DOCUMENTS

| | | | |
|---|---|---|---|
| 2,437,532 A | * 3/1948 | Huffman | 196/28 |
| 2,799,661 A | * 7/1957 | De Rosset | 252/465 |
| 2,960,545 A | 11/1960 | Seubold, Jr. | 260/672 |
| 3,502,595 A | 3/1970 | Johnson et al. | 252/437 |
| 3,617,528 A | * 11/1971 | Hilfman | 208/216 |
| 3,651,163 A | 3/1972 | Radford et al. | 260/672 R |
| 3,679,768 A | 7/1972 | Kmecak et al. | 585/489 |
| 3,686,340 A | 8/1972 | Patrick et al. | 260/672 R |
| 3,694,485 A | * 9/1972 | Drinkard, Jr. et al. | 260/465.8 R |
| 3,761,516 A | * 9/1973 | Khoobiar | 260/530 N |
| 3,840,473 A | * 10/1974 | Beuther et al. | 252/439 |
| 3,923,639 A | 12/1975 | Ciric | 208/111 |
| 3,926,845 A | * 12/1975 | Cichowski | 252/432 |
| 3,954,670 A | 5/1976 | Pine | 252/432 |
| 3,980,586 A | 9/1976 | Mitchell | 252/455 R |
| 3,992,468 A | * 11/1976 | Cosyns et al. | 260/672 R |
| 3,997,431 A | * 12/1976 | Beuther et al. | 208/216 |
| 4,024,052 A | * 5/1977 | Antos | 208/139 |
| 4,046,714 A | * 9/1977 | O'Hara | 252/455 R |
| 4,078,990 A | 3/1978 | Brennan et al. | 208/64 |
| 4,080,286 A | * 3/1978 | Yanik et al. | 208/216 |
| 4,153,580 A | * 5/1979 | Hausberger et al. | 252/462 |
| 4,269,813 A | 5/1981 | Klotz | 423/277 |
| 4,456,699 A | * 6/1984 | Hensley, Jr. et al. | 502/208 |
| 4,483,767 A | 11/1984 | Antos et al. | 208/138 |
| 4,513,097 A | * 4/1985 | Angmorter et al. | 502/211 |
| 4,677,240 A | 6/1987 | Carlson et al. | 585/488 |
| 4,684,617 A | 8/1987 | Lok et al. | 502/214 |
| 4,687,568 A | * 8/1987 | Kukes et al. | 208/251 H |
| 4,689,314 A | * 8/1987 | Martinez et al. | 502/210 |
| 4,711,869 A | 12/1987 | Cullo et al. | 502/339 |
| 4,778,779 A | * 10/1988 | Murrell et al. | 502/263 |
| 4,786,404 A | * 11/1988 | Kemp | 208/217 |
| 4,818,743 A | * 4/1989 | Simpson et al. | 502/211 |
| 4,861,746 A | * 8/1989 | Oishi et al. | 502/314 |
| 5,164,354 A | * 11/1992 | Aldridge et al. | 502/220 |
| 5,198,100 A | * 3/1993 | Aldridge et al. | 208/89 |
| 5,453,411 A | * 9/1995 | Dai et al. | 502/315 |
| 5,714,659 A | * 2/1998 | Wu et al. | 585/483 |
| 5,714,660 A | * 2/1998 | Wu et al. | 585/488 |
| 5,945,575 A | * 8/1999 | Sigwart et al. | 585/531 |
| 6,037,302 A | * 3/2000 | Wu et al. | 502/208 |

OTHER PUBLICATIONS

Oil & Gas Journal, Oct. 11, 1993, pp. 58–59.

* cited by examiner

Primary Examiner—Stanley S. Silverman
Assistant Examiner—Cam N. Nguyen
(74) Attorney, Agent, or Firm—McDermott, Will & Emery

(57) ABSTRACT

A catalyst composition and a process for hydrodealkylating a $C_9+$ aromatic compound such as, for example, 1,2,4-trimethylbenzene to a $C_6$ to $C_8$ aromatic hydrocarbon such as a xylene are disclosed. The composition comprises an alumina, a metal oxide, and a coke suppressor selected from the group consisting of silicon oxides, phosphorus oxides, boron oxides, magnesium oxides, tin oxides, titanium oxides, zirconium oxides, molybdenum oxides, germanium oxides, indium oxides, lanthanum oxides, cesium oxides, and combinations of any two or more thereof. The process comprises contacting a fluid which comprises a $C_9+$ aromatic compound with the catalyst composition under a condition sufficient to effect the conversion of a $C_9+$ aromatic compound to a $C_6$ to $C_8$ aromatic hydrocarbon.

14 Claims, No Drawings

CATALYST COMPOSITION AND PROCESSES THEREFOR AND THEREWITH

This application is a continuation-in-part of application Ser. No. 08/697,767, filed Aug. 29, 1996, now abandoned.

FIELD OF THE INVENTION

This invention relates to a catalyst composition useful for converting a $C_9+$ aromatic compound to a $C_6$ to $C_8$ aromatic hydrocarbon and to a process for using the composition in a hydrodealkylation process.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the aromatization of gasoline to aromatic hydrocarbons by catalytic cracking in the presence of a catalyst. The aromatic hydrocarbons produced by the aromatization process include $C_6$ to $C_8$ hydrocarbons such as benzene, toluene and xylenes (hereinafter collectively referred to as BTX) which can be useful feedstocks for producing various organic compounds and polymers. However, heavier, less useful aromatic compounds are also produced during the aromatization process. It is, therefore, highly desirable to convert these compounds to the more useful BTX.

Furthermore, a catalyst used in the hydrodealkylation of these heavier aromatic compounds is generally deactivated in a rather short period because of depositions of carbonaceous material such as, for example, coke on the surface of the catalyst.

Accordingly, there is an ever-increasing need to develop a catalyst and a process for converting these heavier and less useful aromatic compounds (mainly trimethyl- and tetramethylbenzenes) to the more valuable BTX hydrocarbons (hereinafter referred to as hydrodealkylation process) and, in the meantime, for suppressing the coke formation. Such development would also be a significant contribution to the art and to the economy.

SUMMARY OF THE INVENTION

An object of this invention is to provide a catalyst composition which can be used to convert a $C_9+$ aromatic compound to a $C_6$ to $C_8$ aromatic hydrocarbon. Also an object of this invention is to provide a process for producing the catalyst composition. Another object of this invention is to provide a process which can employ the catalyst composition to convert $C_9+$ aromatic compounds to $C_6$ to $C_8$ aromatic compounds. An advantage of the catalyst composition is that it decreases coke deposits thereon and exhibits high hydrodealkylation activity, satisfactory selectivity to xylenes, and good stability. Other objects and advantages will becomes more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition is a metal oxide-promoted alumina having incorporated therein a coke suppressor wherein the metal of the metal oxide is selected from the group consisting of cobalt, molybdenum, nickel, rhodium, palladium, platinum, chromium, tungsten, and combinations of any two or more thereof.

According to a second embodiment of the invention, a process for producing a composition which can be used as catalyst in a hydrodealkylation process is provided. The process comprises (1) contacting a metal oxide-promoted alumina with a coke suppressor precursor selected from the group consisting of silicon-containing compounds, phosphorus-containing compound, boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof under a condition sufficient to incorporate the coke suppressor into the metal oxide-promoted alumina to form a modified metal oxide-promoted alumina; and (2) calcining the modified metal oxide-promoted alumina under a condition sufficient to convert the coke suppressor precursor to its oxide form wherein the amount of coke suppressor precursor is the amount that is sufficient to be converted to a coke-suppressing amount when said composition is used in a hydrodealkylation process.

According to a third embodiment of the present invention, a process which can be used for converting a $C_9+$ aromatic compound to a $C_6$ to $C_8$ aromatics compound is provided which comprises, consists essentially of, or consists of, contacting a fluid which comprises a $C_9+$ aromatic compound, optionally in the presence of an insert fluid such as a hydrogen-containing fluid, with a catalyst composition which is the same as disclosed above in the first embodiment of the invention under a condition effective to convert a $C_9+$ aromatic compound to an aromatic hydrocarbon containing 6 to 8 carbon atoms per molecule.

DETAILED DESCRIPTION OF THE INVENTION

According to the first embodiment of the invention, a composition which can be used as catalyst in a hydrodealkylation process for converting a $C_9+$ aromatic compound to a $C_6$ to $C_8$ aromatic hydrocarbon is provided. The composition comprises, consists essentially of, or consists of, a metal oxide-promoted alumina having incorporated therein, or impregnated thereon, a coke suppressor selected from the group consisting of silicon oxides, phosphorus oxides, boron oxides, magnesium oxides, tin oxides, titanium oxides, zirconium oxides, molybdenum oxides, germanium oxides, indium oxides, lanthanum oxides, cesium oxides, and combinations of any two or more thereof wherein the coke suppressor is present in the composition in a coke-suppressing amount to suppress coke formation or deposition on the surface of the composition when the composition is used in a hydrodealkylation process. It is most preferred that the composition is substantially free of tin oxides, lead oxides, any Group VIB metal phosphate and any Group VIII metal phosphate.

According to the first embodiment of the invention, the weight ratio of the coke suppressor to the metal oxide-promoted alumina can be any ratio so long as the ratio can suppress or reduce the formation or deposition of coke on an alumina catalyst during the hydrodealkylation process for converting of a $C_9+$ aromatic compound to a $C_6$ to $C_8$ aromatic hydrocarbon. Generally, the ratio can be in the range of from about 0.0001:1 to about 1:1, preferably about 0.0005:1 to about 1:1, more preferably about 0.001:1 to about 0.8:1 and most preferably from 0.005:1 to 0.5:1 for an effective dehydroalkylation conversion and coke reduction or suppression. Alternatively, the coke suppressor can be present in the catalyst composition in the range of from about 0.01 to about 50, preferably about 0.05 to about 50, more preferably about 0.1 to about 45, and most preferably 0.5 to 33 grams per 100 grams of the catalyst composition.

Any metal oxide-promoted alumina which is known to one skilled in the art to be capable of catalyzing a hydrodealkylation of a $C_9+$ aromatic compound to a $C_6$ to $C_8$ aromatic hydrocarbon can be employed in the present invention. The alumina can be $\alpha$-alumina, $\beta$-alumina, $\gamma$-alumina, and combinations of any two or more thereof. The presently preferred alumina is $\gamma$-alumina having a surface area in the range of from about 40 to about 300 $m^2/g$, a total pore volume in the range of from about 0.1 to about 1.

Any metal oxide that, when incorporated into an alumina, is capable of promoting the hydrodealkylation of a $C_9+$ aromatic compound to a $C_6$ to $C_8$ aromatic hydrocarbon be employed in the invention. Presently, it is preferred that the metal oxide is selected from the group consisting of cobalt oxides, molybdenum oxides, nickel oxide, rhodium oxides, palladium oxides, platinum oxides, chromium oxides, tungsten oxides, and combinations of any two or more thereof wherein the oxidation state of the metal can be any available oxidation state. For example, in the case of a cobalt oxide, the oxidation state of cobalt can be either 2 or 3. The presently preferred metal oxide-promoted alumina is $Co/Mo/Al_2O_3$, $Ni/Mo/Al_2O_3$, or combinations of any two or more thereof wherein the $Co/Mo/Al_2O_3$ denotes an alumina promoted with both a cobalt oxide and a molybdenum oxide and $Ni/Mo/Al_2O_3$ denotes an alumina promoted with both a nickel oxide and a molybdenum oxide. These metal oxide-promoted aluminas are commercially available. The weight percent (%) of a metal oxide to the catalyst composition can be any weight % so long as such weight % can be effective on a hydrodealkylation process. The weight % can be in the range of from about 0.1% to about 60%, preferably about 0.5 to about 50%, and most preferably 1 to 40%. If a combination of metal oxides is employed, the molar ratio of the second metal oxide, or the third metal oxide, or the fourth metal oxide to the first metal oxide can be in the range of about 0.01:1 to about 100:1.

According to the present invention, any coke suppressor that, as compared to use of a metal oxide-promoted alumina only, can effect the reduction of coke deposition on the metal oxide-promoted alumina during the conversion of a $C_9+$ aromatic compound to a $C_6$ to $C_8$ aromatic hydrocarbon can be employed. Presently it is preferred that the coke suppressor is selected from the group consisting of silicon oxides, phosphorus oxides, boron oxides magnesium oxides, tin oxides, titanium oxides, zirconium oxides, molybdenum oxides, germanium oxides, indium oxides, lanthanum oxides, cesium oxides, and combinations of any two or more thereof. It is most preferred that the coke suppressor is selected from the group consisting of silicon oxides, phosphorus oxides, and combinations thereof, and that the coke suppressor is substantially free of tin oxide and lead oxide.

Any methods known to one skilled in the art for incorporating a compound or a portion thereof into an alumina such as, for example, impregnation or extrusion can be employed for producing the composition of the present invention. However, it is presently preferred the composition be produced by the process disclosed in the second embodiment of the invention.

A metal oxide-promoted alumina is generally first treated with a coke suppressor precursor. According to the second embodiment of the present invention, any coke suppressor precursor which can be converted to a coke suppressor, as disclosed in the first embodiment of the invention, that, as compared to use of a metal oxide-promoted alumina only, can effect the reduction of coke during a hydrodealkylation process can be employed. Presently it is preferred that a coke suppressor precursor be selected from the group consisting of silicon-containing compounds, phosphorus-containing compounds, boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof. It is most preferred that the coke suppressor precursor is selected from the group consisting of silicon-containing compounds, phosphorus containing compounds, and combinations thereof, and that the coke suppressor precursor is substantially free of tin-containing compounds and lead containing compounds.

Generally any silicon-containing compounds which can be converted to a silicon oxide that are effective to enhance hydrodealkylation of a $C_9+$ aromatic compound when used with a metal oxide-promoted alumina can be used in the present invention. Examples of suitable silicon-containing compounds can have a formula of $(R)(R)(R)Si-(O_mSi(R)(R))_nR$ wherein each R can be the same or different and is independently selected from the group consisting of alkyl radicals, alkenyl radicals, aryl radicals, alkaryl radicals, aralkyl radicals, and combinations of any two or more thereof; m is 0 or 1; and n is 1 to about 10 wherein each radical can contain 1 to about 15, preferably 1 to about 10 carbon atoms per radical. Specific examples of such polymers include, but are not limited to, silicon-containing polymers such as poly(phenylmethylsiloxane), poly (phenylethylsiloxane), poly(phenylpropylsiloxane), hexamethyldisiloxane, decamethyltetrasiloxane, diphenyltetramethyldisiloxane, and combinations of any two or more thereof. Other silicon-containing compounds include organosilicates such as, for example, tetraethyl orthosilicate. A number of well known silylating agents such as trimethylchlorosilane, chloromethyldimethylchlorosilane, N-trimethylsilylimidazole, N,O-bis(trimethylsilyl) acetimide, N-methyl-N-trimethylsilyltrifluoroacetamie, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, {3-(2-aminoethyl) aminopropyl}trimethoxysilane, cyanoethyltrimethoxysilane, aminopropyltriethoxysilane, phenyltrimethoxysilen, (3-chloropropyl)trimethoxysilane, (3-mercaptopropyl)trimethoxysilane, (3-glycidoxypropyl) trimethoxysilane, vinyltris($\beta$-methoxyethoxy)silane, ($\gamma$-methacryloxypropyl)trimethoxysilane, vinylbenzyl cationic silane, (4-aminopropyl)triethoxysilane, {$\gamma$-($\beta$-aminoethylamino)propyl}trimethoxysilane, ($\gamma$-glycidoxypropyl)trimethoxysilane, {$\beta$-(3,4-epoxycyclohexyl)ethyl}trimethoxysilane, ($\beta$-mercaptoethyl)trimethoxysilane, ($\gamma$-chloropropyl) trimethoxysilane, and combinations of any two or more thereof can also be employed. The presently preferred silicon-containing compounds are tetraethyl orthosilicate and poly(phenylmethyl) siloxane.

Similarly, any phosphorus-containing compounds that, when impregnated onto or incorporated into a metal oxide-promoted alumina can be converted into a phosphorus oxide, are capable of reducing coke deposition on a metal oxide-promoted alumina, as compared to the use of the metal oxide-promoted alumina only, can be used in the present invention. Examples of suitable phosphorus-containing compounds include, but are not limited to, phosphorus pentoxide, phosphorus oxychloride, phosphoric acid, phosphines having the formula of $P(OR)_3$, $P(O)(OR)_3$, $P(O)(R)(R)(R)$, $P(R)(R)(R)$, and combinations of any two or more thereof wherein R is the same as that disclosed above. It is most preferred that the phosphorous-containing compound is substantially free of any Group VIB metal phosphate and is substantially free of any Group VIII metal phosphate.

According to the present invention, any boron-containing compound which, upon being incorporated into a metal oxide-promoted alumina can be converted into a boron oxide can be used in the present invention. Examples of suitable boron-containing compounds include, but are not limited to boric acid, borane-ammonium complex, boron trichloride, boron phosphate, boron nitride, triethyl borane, trimethyl borane, tripropyl borane, trimethyl borate, triethyl borate, tripropyl borate, trimethyl boroxine, triethyl boroxine, tripropyl boroxine, and combinations of any two or more thereof.

Examples of suitable magnesium-containing compounds include, but are not limited to, magnesium formate, magnesium acetate, magnesium bromide, magnesium bromide diethyl etherate, magnesium chloride, magnesium fluoride, magnesium nitrate, magnesium sulfate, dibutyl magnesium, magnesium methoxide, and combinations of any two or more thereof.

Similarly, examples of suitable tin-containing compound include, but are not limited to, stannous acetate, stannic acetate, stannous bromide, stannic bromide, stannous chloride, stannic chloride, stannous oxalate, stannous sulfate, stannic sulfate, stannous sulfide, and combinations of any two or more thereof.

Examples of suitable titanium-containing compounds include, but are not limited to, titanium zinc titanate, lanthanum titanate, titanium tetramides titanium tetramercaptides, titanium tetrabutoxide, titanium tetramethoxides, titanium tetraethoxide, titanium tetrapropoxide, titanium tetrachloride, titanium trichloride, titanium bromides, and combinations f any two or more thereof.

Similarly, examples of suitable zirconium-containing compounds include, but are not limited to, zirconium acetate, zirconium formate, zirconium chloride, zirconium bromide, zirconium butoxide, zirconium tert-butoxide, zirconium chloride, zirconium citrate, zirconium ethoxide, zirconium methoxide, zirconium propoxide, and combinations of any two or more thereof.

Suitable molybdenum-containing compounds include, but are not limited to, molybdenum(III) chloride, molybdenum(II) acetate, molybdenum(IV) chloride, molybdenum(V) chloride, molybdenum(VI) fluoride, molybdenum(VI) oxychloride, molybdenum(IV) sulfide, ammonium heptamolybdate(VI) and combinations of two or more thereof.

Examples of suitable germanium-containing compounds include, but are not limited to, germanium chloride, germanium bromide, germanium ethoxide, germanium fluoride, germanium iodide, germanium methoxide, and combinations of any two or more thereof. Examples of suitable indium-containing compounds include, but are not limited to indium acetate, indium bromide, indium chloride, indium fluoride, indium iodide, indium nitrate, indium phosphide, indium selenide, indium sulfate, and combinations of any two or more thereof. Examples of suitable lanthanum-containing compounds include, but are not limited to, lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, tanthanum titanate, and combinations of any two or more thereof.

Generally, a metal oxide-promoted alumina can be combined with such coke suppressor precursor in any suitable weight ratios which would result in the weight ratios of a coke suppressor to a metal oxide-promoted alumina disclosed in the first embodiment of the invention. Presently it is preferred that such combination be carried out in a suitable liquid, preferably an aqueous medium, to form an incipient wetness metal oxide-promoted alumina-precursor mixture. Upon the metal oxide-promoted alumina and the precursor are well mixed, the metal oxide-promoted alumina-precursor mixture is subjected to calcination under a condition that can include a temperature in the range of from about 300° C. to about 1000° C., preferably about 350° C. to about 750° C., and most preferably 400° C. to 650° C. under a pressure in the range of from about 1 to about 10, preferably about 1 atmospheres for a period in the range of from about 1 to about 30, preferably about 1 to about 20, and most preferably 1 to 15 hours.

Upon completion of incorporating the coke suppressor onto the metal oxide-promoted alumina a coke suppressor-incorporated alumina is formed. The coke suppressor-incorporated alumina can be, if desired, pretreated with a reducing agent before being used in a hydrodealkylation process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process useful for converting a $C_9+$ aromatic compound to a $C_6$ to $C_8$ aromatic hydrocarbon comprises, consists essentially of, or consists of contacting a fluid stream comprising a $C_9+$ aromatic compound and, optionally, in the presence of an inert fluid such as, for example, hydrogen-containing fluid, with a catalyst composition under a condition sufficient to effect the conversion of a $C_9+$ aromatic compound to a $C_6$ to $C_8$ aromatic hydrocarbon. The inert fluid can be nitrogen, helium, argon, carbon dioxide, neon, steam, and combinations of any two or more thereof. The presently preferred inert fluid is a hydrogen-containing fluid. The inert fluid can also be fed separately into contact with a $C_9+$ aromatic compound and a catalyst. The catalyst composition is the same as that disclosed in the first embodiment of the invention.

The term "fluid" is used herein to denote gas, liquid, vapor, or combinations of two or more thereof. The term "$C_9+$ aromatic compound" is referred to, unless otherwise indicated, as a substituted aromatic compound containing at least 9 carbon atoms per molecule. Preferably the substituted aromatic compound has the formula of $R'_qAr$ wherein each $R'$ is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is a phenyl group. More preferably $R'$ is an alkyl radical having 1 to about 10 carbon atoms and the aromatic compound has 9 to about 16 carbon atoms per molecule. Most preferably the aromatic compound contains 9 to 12 carbon atoms per molecule.

Any fluid which contains a $C_9+$ aromatic compound as disclosed above can be used as the feed for the process of this invention. The origin of this fluid feed is not critical. However, a preferred fluid feed is a $C_9+$ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, and 1,3-diethylbenzene can also be present in the fluid. Benzene, toluene, ethylbenzene and xylenes are generally substantially absent from the fluid, i.e., the amount of each of these aromatic hydrocarbons is less than about 0.1 weight %. Thus, there is no significant alkylation of these lower aromatic hydrocarbons by the $C_9+$ aromatic compound, i.e., no significant transalkylation occurs as a side-reaction in the process of this invention. To demonstrate the process of the invention, a trimethyl benzene such as 1,2,4-trimethylbenzene was used.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid containing a $C_9+$ aromatic compound, in the presence or absence of a hydrogen-containing fluid, with a catalyst composition can be carried out in any technically suitable manner, in batch, semicontinuous, or continuous process under a condition effective to convert a $C_9+$ aromatic compound to a $C_6$ to $C_8$ aromatic hydrocarbon. Generally, a fluid containing a $C_9+$ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9+$ aromatic compound fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3 H_2/ft^3$ catalyst/hour. The preferred molar ratio of $H_2$ to the $C_9+$ aromatic compound can be in the range of from about 0.01:1 to about 20:1, preferably about 0.1:1 to about 10:1, and most preferably 0.5:1 to 5:1. Generally, the pressure can be in the range of from about 30 to about 1000 psig, preferably about 50 to about 750 psig, and most preferably 200 to 600 psig, and the temperature is about 250 to about 1,000° C., preferably about 350 to about 800° C., and most preferably 400° C. to 650° C.

The process effluent generally contains a heavies fraction of unconverted $C_9+$ aromatics and other heavy ($C_9+$) aromatic compounds which may have been formed by side-reactions (such as isomerization); a lights fraction of alkanes, mainly methane, ethane, propane, n-butane, isobutane, and minor amounts (about 0.1 to about 5 weight %) of $C_5$ and $C_6$ alkanes such as, for example, isopentane and n-pentane; and a BTX aromatic hydrocarbons fraction (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor described above, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes) involving transalkylation benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400 to about 650° C., followed by a treatment with a reducing agent such as, for example, with hydrogen gas at a temperature of about 400 to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the preparation of catalyst compositions of the invention and the use of the composition in a hydrodealkylation process.

An alumina promoted with NiO and $MoO_3$ (Ni/Mo/$Al_2O_3$), obtained as 1/16 inch extrudates from Katalco Catalyst Company, having the designation of 52-2 was used. First, 100 g of the Ni/Mo/$Al_2O_3$ was calcined at 525° C. for 6 hours to produce 90.32 g of calcined Ni/Mo/$Al_2O_3$.

Secondly, a portion of the calcined Ni/Mo/$Al_2O_3$ (10.0 g) was well mixed with 5.14 g of a 50 weight % tetraethyl orthosilicate (TEOS) in cyclohexane followed by calcining the resulting mixture in air in a furnace at 538° C. for 6 hours to produce 10.67 g of a silicon oxide-incorporated Ni/Mo/$Al_2O_3$ containing 5 weight % silicon oxide by calculation. In a separate run, a similarly obtained silicon-oxide incorporated Ni/Mo/$Al_2O_3$ (10.67 g) was similarly treated with 3.23 g of 50 weight % TEOS followed by calcining at 538° C. in air for 6 hours to product 7.68 g of a silicon oxide-incorporated Ni/Mo/$Al_2O_3$ containing 10 weight % silicon oxide by calculation.

These silicon oxide-incorporated, Ni/Mo-promoted aluminas were then employed, according to the third embodiment of the invention, in a hydrodealkylation process for converting 1,2,4-trimethylbenzene to BTX. The 1,2,4-trimethylbenzene was obtained from Phillips Petroleum Company, Bartlesville, Okla., and was employed as feedstock. The hydrodealkylation process was carried out as follows.

A stainless-steel reactor tube (inner diameter 0.75 inch; length: 20 inches) was filled with a 20 ml bottom layer of Alundum® alumina (inert, low surface area alumina), one of the catalysts (in 1/16 inch extrudates) in the center position 5 ml, and a 20 ml top layer of Alundum® alumina. The catalysts were pretreated with hydrogen (260 ml/minute) at 575° C. (starting at 25° C. then ramping at 10° C./min) for one hour. The 1,2,4-trimethylbenzene feed was then introduced into the reactor at a rate of 20 milliliters/hour (WHSV=5.6), together with hydrogen gas at a rate of 260 ml of $H_2$/hours (molar ratio of $H_2$ to 1,2,4-trimethylbenzene was 5). The reaction temperature was about 575° C., and the reaction pressure was 500 psig. The reactor effluent was cooled and analyzed with an on-line gas chromatograph at intervals of about 1 hour. The results are shown in Table I.

TABLE I

| Ni/Mo/$Al_2O_3$ incorporated with | Catalyst Weight (g) | Reaction Temp (° C.) | Time (hr) | Reactor Effluent (wt %)[b] | | | | | |
|---|---|---|---|---|---|---|---|---|---|
| | | | | Lights | BTX | Xyl | $C_9$+ | Conversion % | Coke |
| None | 3.16 | 580 | 6.30 | 9.5 | 59.4 | 30.1 | 31.1 | 70.8 | 25.54 |
| TEOS (5)[a] | 3.44 | 581 | 6.15 | 10.0 | 53.3 | 29.8 | 36.7 | 73.0 | 14.53 |
| TEOS (10) | 3.62 | 578 | 6.22 | 9.6 | 55.7 | 32.1 | 34.7 | 77.4 | 8.11 |

[a]The numbers shown are weight % of silicon oxide content, in addition to that originally present in the Ni/Mo/$Al_2O_3$ catalyst, and were determined by weight increase after calcining.
[b]The values presented, except conversion, are weight percent. Conversion denotes percent of 1, 2, 4-trimethylbenzene that was converted at time shown. Xyl denotes the total weight % of all xylenes. The lights fraction included hydrocarbons shown in the text. The coke was determined at the end of a 7-hour run by removing the catalyst from the reactor and determined with a thermal gravimetric analyzer (TGA), manufactured by TA Instruments, New Castle, Delaware.

The results shown in Table I indicate that without TEOS treatment, the catalyst was heavily covered with coke (25.54%). The TEOS-treated catalyst significantly reduced the coke deposition.

EXAMPLE II

This example illustrates that other silicon-containing compounds can also be used to incorporate a silicon oxide into a metal oxide-promoted alumina and that the thus-produced catalysts are also effective on reducing coke depositions.

The metal oxide promoted alumina was Co/Mo/$Al_2O_3$, obtained from Haldor-Topsoe, Lyngby, Denmark, as 1/20 inch extrudates, having the designation of TK-75, in which the metal oxide was a combination of CoO and $MoO_3$. This Co/Mo/$Al_2O_3$ (50 g) was calcined in air in a furnace for 3 hours at 500° C. to produce 46.23 g of calcined Co/Mo/$Al_2O_3$ (catalyst A).

A portion (10 g) of the calcined Co/Mo/$Al_2O_3$ was then well mixed with 5.38 of a 50 weight % poly(phenylmethyl) siloxane (PPMS) in cyclohexane (obtained from Dow Chemical, Midland, Mich.). The mixture was calcined at 538° C. in a furnace to produce 10.77 g of silica-incorporated Co/Mo/$Al_2O_3$. A portion (7.18 g) of this silicon oxide-incorporated Co/Mo/$Al_2O_3$ was further blended with 3.23 g of 50 weight % PPMS followed by calcination at 538° C. for 6 hours to produce 7.67 g of a silicon oxide-incorporated Co/Mo/$Al_2O_3$ containing 14 weight % of silicon oxide by calculation (catalyst B).

In a separate run, 3.83 g of catalyst B was further blended with 1.59 g of 50 weight % PPMS followed by calcination at 538° C. for 6 hours to prepare 4.0 g of a silicon oxide-impregnated Co/Mo/$Al_2O_3$ containing a calculated 18.8 weight % silicon oxide (catalyst C).

Catalysts A, B and C were then used in a hydrodealkylation process to convert 1,2, 4-trimethylbenzene to BTX.

The hydrodealkylation process was identical to that disclosed in Example I except the catalysts used. The results are shown in Table II.

TABLE II[a]

| Catalyst | Catalyst Weight (g) | Reaction Temp (° C.) | Time (hr) | Reactor Effluent (wt %) | | | | Conversion % | Coke |
|---|---|---|---|---|---|---|---|---|---|
| | | | | Lights | BTX | Xyl | $C_9+$ | | |
| A | 2.83 | 522 | 6.07 | 14.7 | 20.6 | 15.9 | 64.7 | 37.8 | 1.52 |
| B | 3.40 | 529 | 6.30 | 11.4 | 33.9 | 26.9 | 54.7 | 67.8 | 0.56 |
| C | 3.60 | 526 | 6.37 | 10.9 | 37.2 | 29.4 | 51.9 | 70.6 | 0.23 |

[a]See footnotes in Table I.

The results shown in Table II again demonstrate that treatment of $Co/Mo/Al_2O_3$ with a silicon-containing compound resulted in significantly decreased coke formation when the catalyst were used in a hydrodealkylation process. The results also indicate that silicon oxide-incorporated $Co/Mo/Al_2O_3$ increased the conversion of 1,2,4-trimethylbenzene, the production of BTX, and the selectivity to xylenes.

EXAMPLE III

This example illustrates other metal oxide-promoted alumina compositions of the invention and processes therewith.

The catalyst compositions were prepared by the same procedure as that disclosed in Example II except that proper amounts of diluted phosphoric acid ($H_3PO_4$) were used in place of a PPMS to treat catalyst A to produce phosphorus oxide-containing $Co/Mo/Al_2O_3$.

In one preparation, 3.5 g of catalyst A (Example II) was mixed with 2.95 g of 10 weight % $H_3PO_4$. The mixture was calcined at 538° C. in air for 6 hours to prepare 3.71 g of a phosphorus oxide-incorporated $Co/Mo/Al_2O_3$ having 5.8 weight % (by calculation) of phosphorus oxide (catalyst D). In a separate preparation, 3.5 g of catalyst C was mixed with 2.81 g of 25 weight % $H_3PO_4$ and then calcined at 538° C. for 6 hours to prepare 4.01 g of a phosphorus oxide-incorporated $Co/Mo/Al_2O_3$ containing 12.7% phosphorus oxide by calculation (catalyst E). In a further preparation, 3.53 g of catalyst C was impregnated with 2.99 g of 50 weight % $H_3PO_4$ followed by calcination to prepare a phosphorus oxide-incorporated ferrierite having a calculated 23.4 weight % phosphorus oxide (catalyst F).

The hydrodealkylation process for converting 1,2,4-trimethylbenzene to BTX was the same as that disclosed in Example I except the catalysts used were those prepared in this example. The results are shown in Table III below.

Table III shows that phosphorus oxide-incorporated $Co/Mo/Al_2O_3$ significantly decreased the lights in the product stream from 14.96% (catalyst A) to as low as 0.81% (catalyst F). Additionally, similar to the results presented in Tables I and II, the coke formation was reduced from as high as 1.52 weight to as low as 0.12 weight %. It appears that, from the results shown in Table III, the best range for phosphorus oxide is in the range of from about 12 to about 23 weight %.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A composition comprising a metal oxide-promoted alumina treated with a coke suppressor precursor, said coke suppressor precursor comprises a silicon-containing compound selected from the group consisting of silicon-containing polymers and organosilicates, wherein the thus treated metal oxide promoted alumina has been subjected to calcination conditions.

2. A composition as recited in claim 1 wherein said calcination conditions include a temperature in the range of from about 300° C. to about 1000° C. and a pressure in the range of from about 1 atmosphere to about 10 atmospheres and a time period in the range of from about 1 to about 30 hours.

3. A composition as recited in claim 2 wherein said silicon-containing polymers include those compounds selected from the group consisting of poly(phenylmethylsiloxane), poly(phenylethylsiloxane), poly(phenylpropylsiloxane), hexamethyldisiloxane, decamethyltetrasiloxane, diphenyltetramethyldisiloxane and combinations of any two or more thereof, and wherein said organosilicates include tetraethyl orthosilicate.

4. A composition as recited in claim 3 wherein the amount of coke suppressor precursor combined with said metal TABLE III[a]

| Catalyst | Wt % Phosphorus Oxide | Catalyst (g) | Reaction Temp (° C.) | Time (hr) | Reaction Effluent (wt %) | | | | |
|---|---|---|---|---|---|---|---|---|---|
| | | | | | Lights | BTX | Xylenes | $C_9+$ | Coke |
| A | 0 | 2.83 | 522 | 6.07 | 14.96 | 20.11 | 15.95 | 65.17 | 1.52 |
| D | 5.8 | 3.08 | 526 | 6.09 | 3.26 | 36.2 | 30.37 | 60.58 | 0.27 |
| E | 12.7 | 3.36 | 531 | 6.47 | 1.63 | 28.8 | 25.17 | 69.56 | 0.12 |
| F | 23.4 | 3.89 | 524 | 6.17 | 0.81 | 22.01 | 18.67 | 76.16 | 0.12 |

[a]See footnote b in Table I.

oxide-promoted alumina in the treatment thereof is such that the amount of coke suppressor present in said composition is in the range of from about 0.01 to about 50 grams per 100 grams of said composition.

5. A composition as recited in claim 4 wherein said metal oxide promoted-alumina is $Co/Mo/Al_2O_3$, $Ni/Mo/Al_2O_3$, or a combination thereof, wherein the $Co/Mo/Al_2O_3$ denotes an alumina promoted with both a cobalt oxide and a molybdenum oxide and $Ni/Mo/Al_2O_3$ denote an alumina promoted with both a nickel oxide and a molybdenum oxide.

6. A composition as recited in claim 5 wherein said silicon-containing polymer is poly(phenylmethysiloxane).

7. A composition comprising a metal oxide-promoted alumina treated with a coke suppressor precursor, said coke suppressor precursor comprises a phosphorus-containing compound capable of being converted into a phosphorus oxide, wherein the treated metal oxide alumina has been subjected to calcination conditions.

8. A composition as recited in claim 7 wherein said calcination conditions include a temperature in the range of from about 300° C. to about 1000° C. and a pressure in the range of from about 1 atmosphere to about 10 atmospheres and a time period in the range of from about 1 to about 30 hours.

9. A composition as recited in claim 7 wherein the amount of cake suppressor precursor combined with said metal oxide-promoted alumina in the treatment thereof is such that the amount of coke suppressor present in said composition is in the range of from about 0.01 to about 50 grams per 100 grams of said composition.

10. A composition as recited in claim 7 wherein said metal oxide-promoted alumina is $Co/Mo/Al_2O_3$, $Ni/Mo/Al_2O_3$, or a combination thereof, wherein the $Co/Mo/Al_2O_3$ denotes an alumina promoted with both a cobalt oxide and a molybdenum oxide and $Ni/Mo/Al_2O_3$ denote an alumina promoted with both a nickel oxide and a molybdenum oxide.

11. A composition consisting essentially of alumina promoted with a metal oxide, said composition is treated with a coke suppressor precursor, said coke suppressor precursor comprises a phosphorus-containing compound capable of being converted into a phosphorus oxide, wherein the treated metal oxide alumina has been subjected to calcination conditions.

12. A composition as recited in claim 11 wherein said calcination conditions include a temperature in the range of from about 300° C. to about 1000° C. and a pressure in the range of from about 1 atmosphere to about 10 atmospheres and a time period in the range of from about 1 to about 30 hours.

13. A composition as recited in claim 11 wherein the amount of coke suppressor precursor combined with said metal oxide-promoted alumina in the treatment thereof is such that the amount of coke suppressor present in said composition is in the range of from about 0.01 to about 50 grams per 100 grams of said composition.

14. A composition as recited in claim 11 wherein said metal oxide promoted alumina is $Co/Mo/Al_2O_3$, $Ni/Mo/Al_2O_3$, or a combination thereof wherein the $Co/Mo/Al_2O_3$ denotes an alumina promoted with both a cobalt oxide and a molybdenum oxide and $Ni/Mo/Al_2O_3$ denotes an alumina promoted with both a nickel oxide and a molybdenum oxide.

* * * * *